United States Patent

Kohno et al.

Patent Number: 5,359,076
Date of Patent: Oct. 25, 1994

[54] CYCLIC AMINOPHENYLACETIC ACID DERIVATIVES, PROCESS FOR PREPARING THE SAME AND IMMUNE RESPONSE MODULATOR HAVING THE SAME AS AN EFFECTIVE INGREDIENT

[75] Inventors: Yasushi Kohno; Katsuya Awano, both of Oyama; Takayoshi Ishizaki, Washimiya; Eisuke Kojima, Koga; Shinji Kudoh, Nogi; Yasuhiko Sakoe; Koji Saito, both of Oyama, all of Japan

[73] Assignee: Kyorin Pharmaceutical Co., Ltd., Tokyo, Japan

[21] Appl. No.: 956,012

[22] PCT Filed: Apr. 15, 1992

[86] PCT No.: PCT/JP92/00476
§ 371 Date: Dec. 9, 1992
§ 102(e) Date: Dec. 9, 1992

[87] PCT Pub. No.: WO92/18482
PCT Pub. Date: Oct. 29, 1992

[30] Foreign Application Priority Data

Apr. 16, 1991 [JP] Japan .................. 3-111000
Apr. 10, 1992 [JP] Japan .................. 4-116730

[51] Int. Cl.$^5$ .............. C07D 215/24; C07D 215/48; C07D 215/16; C07D 215/06
[52] U.S. Cl. ........................ 546/165; 546/14; 546/153; 546/166
[58] Field of Search .......... 546/166, 14, 153, 165; 514/311, 312

[56] References Cited

U.S. PATENT DOCUMENTS 3,778,511 12/1973 Bernasconi .................. 514/311
4,303,590 12/1981 Tanaka et al. .............. 260/410
5,124,325 6/1992 Kojima ...................... 514/224.2
5,281,600 1/1994 Kojima ...................... 546/311

FOREIGN PATENT DOCUMENTS 49-274 1/1974 Japan .
58-116466 7/1983 Japan .

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

The present invention provides novel cyclic aminophenylacetic acid derivatives having modulating action on immune response, their optical isomers, their salts and their preparative processes, and therapeutic agents for autoimmune diseases containing them as effective ingredients, the cyclic aminophenylacetic acid derivatives being represented by a general formula (1)

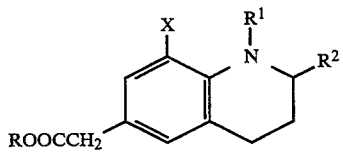

wherein R and $R^1$ each independently denotes hydrogen atom or lower alkyl group having 1 to 3 carbon atoms, $R^2$ denotes a phenyl group (which may be substituted with 1 to 3 groups of halogen atom, methoxy group or their combinations) or trifluoromethyl group, and X denotes a hydrogen atom, lower alkyl group having 1 to 3 carbon atoms, lower alkoxy group having 1 to 3 carbon atoms, cyano group, thiocyano group, trimethylsilylethinyl group, phenyl group (which may be substituted with halogen atom, methoxy group, methyl group or their combinations), carbamoyl group, carboxyl group, lower alkoxycarbonyl group having 1 to 3 carbon atoms, acetyl group, benzoyl group, nitro group, amino group, lower alkanoylamino group having 1 to 3 carbon atoms, benzoylamino group which may be substituted, phenylsulfonylamino group which may be substituted, lower alkylthio group having 1 to 3 carbon atoms, lower alkylsulfinyl group having 1 to 3 carbon atoms, lower alkylsulfonyl group having 1 to 3 carbon atoms or halogen atom.

2 Claims, No Drawings

CYCLIC AMINOPHENYLACETIC ACID DERIVATIVES, PROCESS FOR PREPARING THE SAME AND IMMUNE RESPONSE MODULATOR HAVING THE SAME AS AN EFFECTIVE INGREDIENT

FIELD OF THE INVENTION

The present invention relates to novel cyclic aminophenylacetic acid derivatives having immune response-modulating action, their optical isomers and salts, their preparative processes, and therapeutic agents for autoimmune diseases containing them as effective ingredients.

BACKGROUND

For the therapy of chronic diseases (rheumatoid arthritis and autoimmune diseases) with which the immune response is concerned, anti-inflammatory agents, immunomodulators, etc. are used. The formers are for symptomatic therapy, thus cannot become fundamental therapeutic agents. Whereas, the latters, in which gold salt and D-penicillamine, levamisole, lobenzarit, etc. are known, have attracted an attention for the last several years.

The inventors have also studied diligently for the purpose of developing a more effective and safer antirheumatic agent and have found previously that the cyclic anthranilic acid derivatives have immunomodulatory action and inducing ability for suppressor T cells, and that they have therapeutic effect against rheumatoid arthritis (Japanese Unexamined Patent Publication No. Hei 1-279867). However in cyclic aminophenylacetic acid derivatives, compounds having such action are not known.

In cyclic aminophenylacetic acid derivatives having different substituent from the compounds in this invention, those having anti-inflammatory, antipyretic and analgesic actions are described in Japanese Unexamined Patent Publication No. Sho 58-116466 and U.S. Pat. No. 3,778,511 (1973), but the immuno-modulating action is not referred at all. These publicly known compounds, with which a possibility to cause gastrointestinal injury is suggested, belong to a category of non-steroidal anti-inflammatory drugs having cyclooxygenase-inhibitory action, and their usefulness is not satisfactory from the points of efficacy and toxicity. Moreover, cyclic aminophenylacetic acid derivatives exhibiting monoamineoxydase-inhibitory action are also known (Chemical Abstract, Vol. 64, 1753c (1966), ibid Vol. 70, 10292f(1969)), but these also differ from the compounds of the invention in the structure and action.

DISCLOSURE OF THE INVENTION

As a result of further extensive studies on relating compounds, the inventors have found that novel cyclic aminophenylacetic acid derivatives represented by a general formula (1)

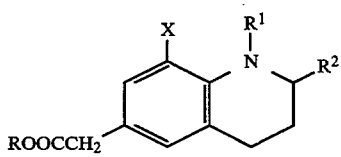
(1)

[wherein R and $R^1$ each independently denotes hydrogen atom or lower alkyl group having 1 to 3 carbon atoms, $R^2$ denotes a phenyl group (which may be substituted with 1 to 3 groups of halogen atom, methoxy group or their combinations) or trifluoromethyl group, and X denotes a hydrogen atom, lower alkyl group having 1 to 3 carbon atoms, lower alkoxy group, having 1 to 3 carbon atoms, cyano group, thiocyano group, trimethylsilylethinyl group, phenyl group (which may be substituted with halogen atom, methoxy group, methyl group or their combinations), carbamoyl group, carboxyl group, lower alkoxycarbonyl group having 1 to 3 carbon atoms, acetyl group, benzoyl group, nitro group, amino group, lower alkanoylamino group having 1 to 3 carbon atoms, benzoylamino group which may be substituted, phenylsulfonylamino group which may be substituted, lower alkylthio group having 1 to 3 carbon atoms, lower alkylsulfinyl group having 1 to 3 carbon atoms, lower alkylsulfonyl group having 1 to 3 carbon atoms, or halogen atom], their optical isomers and their salts have conspicuous modulating action on immune response, have excellent inhibitory action also against acute inflammation, which cannot be seen with conventional immunomodulatory drugs, and yet do not exhibit cyclooxygenase-inhibitory action.

Further, the inventors have found that they exhibit fast-acting and persistent therapeutic effect against adjuvant arthritis being a typical pathologic model of rheumatoid arthritis. Further, the inventors have come to confirm the safety, too, leading to the completion of the invention.

According to the invention, the compounds represented by the general formula (1) can be prepared through processes, for example, as described below.

Namely, by reducing quinoline derivatives represented by a general formula (2)

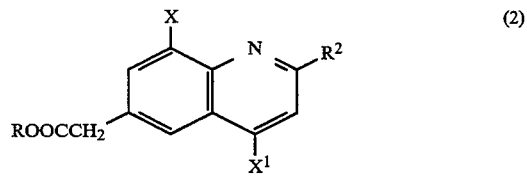
(2)

[wherein R denotes a hydrogen atom or lower alkyl group having 1 to 3 carbon atoms, $R^2$ denotes a phenyl group (which may be substituted with 1 to 3 groups of halogen atom, methoxy group or their combinations) or trifluoromethyl group, X denotes a hydrogen atom, lower alkyl group having 1 to 3 carbon atoms, lower alkoxy group having 1 to 3 carbon atoms, cyano group, thiocyano group, trimethylsilylethinyl group, phenyl group (which may be substituted with halogen atom, methoxy group, methyl group or their combinations), carbomoyl group, carboxyl group, lower alkoxycarbonyl group having 1 to 3 carbon atoms, acetyl group, benzoyl group, nitro group, amino group, lower alkanoylamino group having 1 to 3 carbon atoms, benzoylamino group which may be substituted, phenylsulfonylamino group which may be substituted, lower alkylthio group having 1 to 3 carbon atoms, lower alkyl sulfinyl group having 1 to 3 carbon atoms, lower alkylsulfonyl group having 1 to 3 carbon atoms or halogen atom, and $X^1$ denotes a hydrogen atom, chlorine atom or bromine atom], the inventive compounds represented by a general formula (1a) can be prepared.

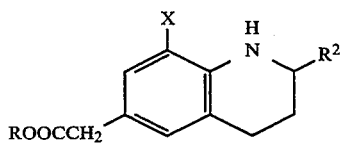

[wherein R, R² and X denote same meanings as above].

This reduction can be carried out at a temperature of ambient temperature to 80° C. and a pressure of atmospheric pressure to 50 kg/cm under hydrogen gas stream in the presence of catalyst for reduction, for example, palladium carbon, dissolving the compounds of the general formula (2) into a suitable solvent, for example, methanol, ethanol, isopropanol or the like. Also, they can be prepared by reacting with sodium borocyanohydride in a suitable solvent, for example, methanol, ethanol, acetic acid or the like.

Moreover, by reacting compounds represented by a general formula (1b)

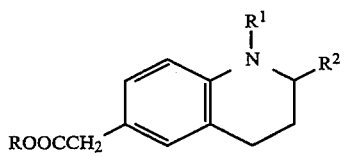

[wherein R, R¹ and R² denote same meanings as above] with a halogenating agent, for example, fluorine, chlorine, bromine, hypohalogenous acid, N-halogenosuccinimide, halogen-pyridine type chlorine complex or the like in an inert solvent, the inventive compounds represented by a general formula (1c) can be prepared.

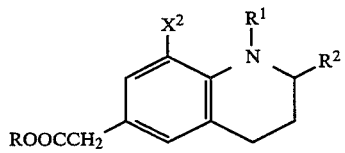

[wherein X² denotes a halogen atom and R, R¹ and R² denote same meanings as above].

Furthermore, by reacting compounds represented by a general formula (1d)

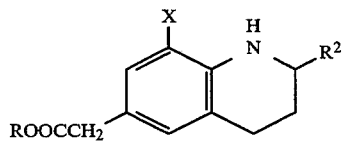

[wherein, R, R² and X denote same meanings as above] with an alkylating agent, for example, halogenated alkyl, alkyl sulfate, alkyl ester of aromatic sulfonic acid or the like in the presence of a deacidifying agent, for example, trialkylamines, pyridine bases, alkali carbonates or the like using a suitable solvent, for example, acetone, acetonitrile, methanol, ethanol, dimethylformamide or the like, or by treating with a mixed reagent of aldehydes with formic acid or catalytic reduction agent, the inentive compounds represented by a general formula (1e) can be prepared.

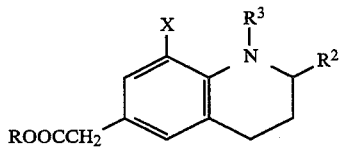

[wherein R³ denotes a lower alkyl group having 1 to 3 carbon atoms and R, R² and X denote same meanings as above].

Next, ester derivatives represented by a general formula (1f)

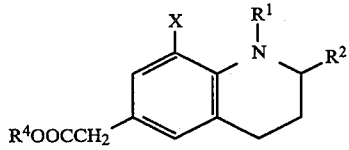

[wherein R⁴ denotes a lower alkyl group having 1 to 3 carbon atoms and R¹, R² and X denote same meanings as above] can be derived easily to the inventive compounds represented by a general formula (1g)

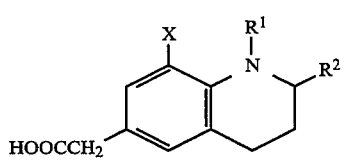

[wherein R¹, R² and X denote same meanings as above] by hydrolyzing with acid or alkali according to usual method.

Besides, the important intermediates of the invention represented by the general formula (2) can be prepared through publicly known process (process A shown below).

On the other hand, compounds, R² being trifluoromethyl group in the compounds represented by the general formula (2), are preferable to be prepared via a process (process B shown below) developed newly by the inventors. Namely, by reacting aminophenylacetic acid derivatives (4) with equimolar or slightly excess alkyl ester of 3-trifluoromethylpropiolic acid (5) at 0° C. to boiling point of solvent used, preferably room temperature in a suitable solvent, for example, methanol, ethanol, isopropanol, acetonitrile, dioxane or the like, alkyl ester of 3-(substituted phenylamino)-3-trifluoromethylacrylic acid (6=6') can be prepared in high yield. In the inventive process, the reaction temperature is milder and the reaction time is also shorter compared with former process (process A). And, it gives less side reaction and higher yield generally. This process is superior especially as a preparative process of compounds, X¹ being lower alkoxy group or lower alkyl group.

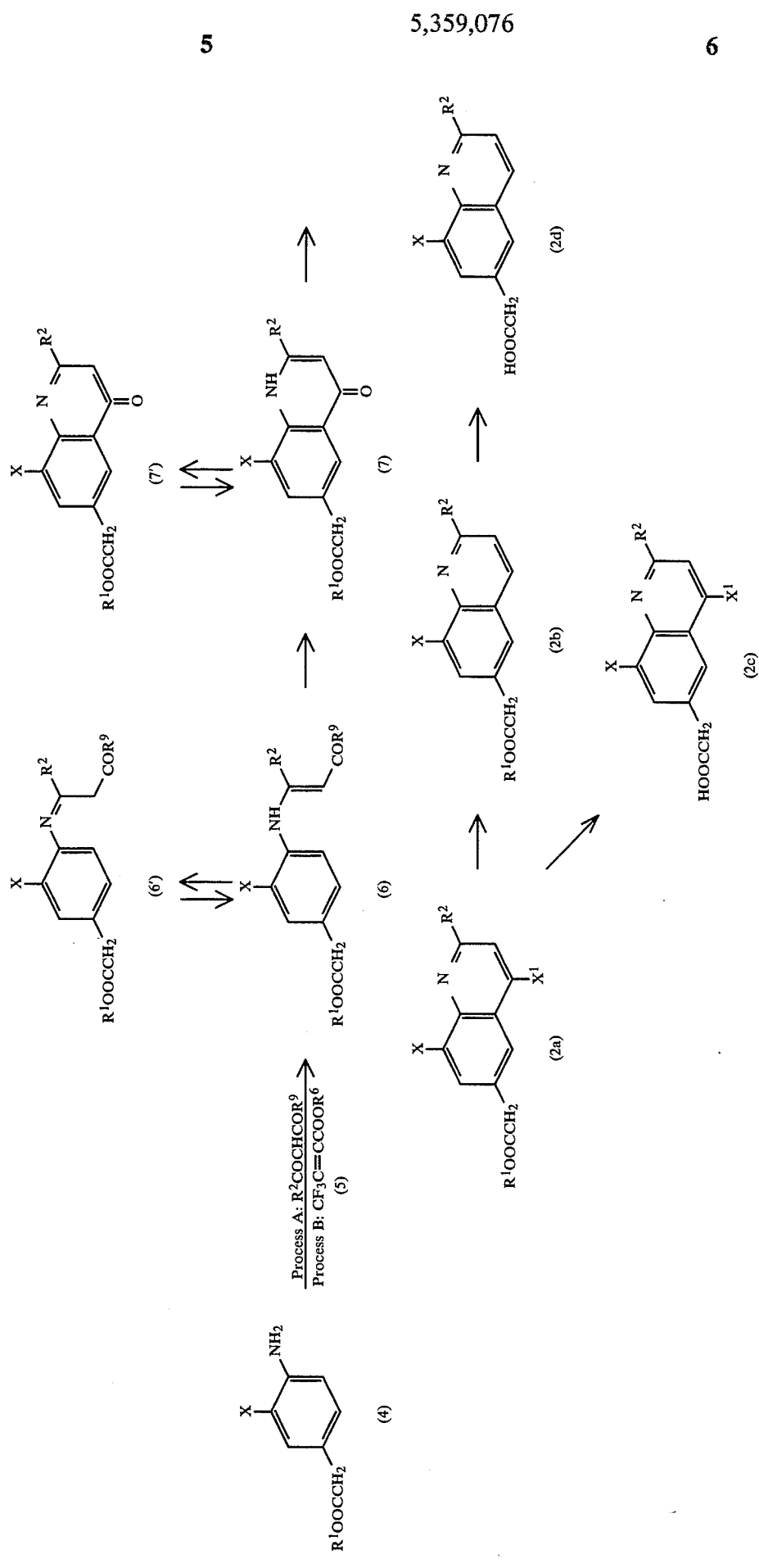

[wherein $R^9$ denotes a lower alkoxy group, benzyloxy group or phenylamino group which may be substituted and $R^2$, $R^4$, X and $X^1$ denote same meanings as above].

Further, some of compounds represented by the general formula (1) can also be prepared through processes illustrated below.

Namely, by reacting compounds represented by a general formula (1h)

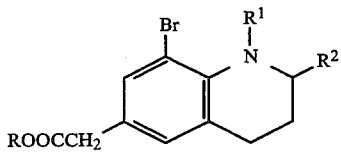

[wherein R, $R^1$ and $R^2$ denote same meanings as above] with a suitable cyanizing agent, for example, copper cyanide, potassium cyanide, sodium cyanide or the like in a suitable solvent, for example, N-methylpyrrolidone, dimethylformamide, pyridine or the like under heating and stirring, the inventive compounds represented by a general formula (1i)

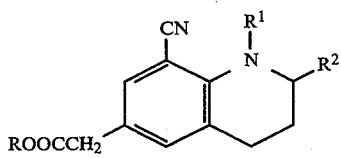

[wherein R, $R^1$ and $R^2$ denote same meanings as above] can be prepared.

Compounds represented by a general formula (1j)

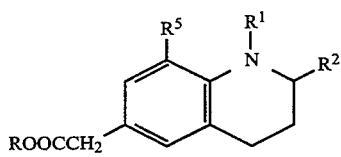

[wherein R, $R^1$ and $R^2$ are same as above and $R^5$ denotes a carbamoyl group, lower alkoxycarbonyl group having 1 to 3 carbon atoms or carboxyl group] can be prepared by acid hydrolyzing the compounds represented by the general formula (1i), for example, by heating and stirring them in polyphosphoric acid, concentrated sulfuric acid or concentrated hydrochloric acid, or by alkali hydrolyzing them in a suitable solvent, for example, ethanol, methanol, dimethyl sulfoxide or the like, for example, by reacting them with sodium hydroxide, potassium hydroxide or the like.

Compounds represented by a general formula (1l)

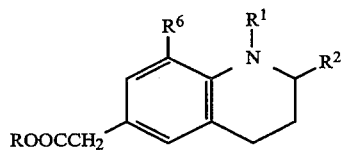

[wherein R, $R^1$ and $R^2$ are same as above and $R^6$ denotes a phenyl group which may be substituted with halogen atom, methoxy group, methyl group of their combinations] can be prepared by heating and stirring the compounds represented by the general formula (1h) with boric acid derivatives represented by a general formula (1k)

[wherein $R^6$ denotes same meaning as above] in an inert solvent in the presence of metal catalyst, preferably tetrakistriphenylphosphine palladium (O) and basic substance under an atmosphere of argon.

Compounds represented by a general formula (1m)

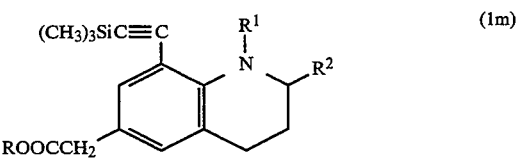

[wherein R, $R^1$ and $R^2$ denote same meanings as above] can be prepared by heating and stirring the compounds represented by the general formula (1h) with trimethylsilylacetylene, triethylamine and copper iodide in a suitable solvent, for example, dimethylformamide, tetrahydrofuran or the like in the presence of bistriphenylphosphine palladium diacetate, bistriphenylphosphine palladium dichloride or the like.

Compounds represented by a general formula (1n)

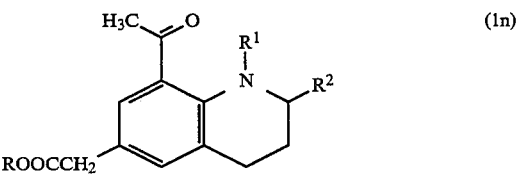

[wherein R, $R^1$ and $R^2$ denote same meanings as above] can be prepared by heating and stirring the compounds represented by the general formula (1m) with concentrated sulfuric acid, mercury sulfate and the like in a suitable solvent, for example, water-containing acetone to hydrate.

By catalytic reduction of compounds represented by a general formula (1o)

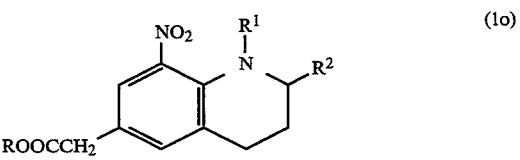

[wherein R, $R^1$ and $R^2$ denote same meanings as above] at atmospheric pressure and room temperature in a suitable solvent, for example, ethanol, methanol, dimethylformamide or the like in the presence of suitable catalyst, for example, 10% palladium carbon under hydrogen gas stream, compounds represented by a general formula (1p)

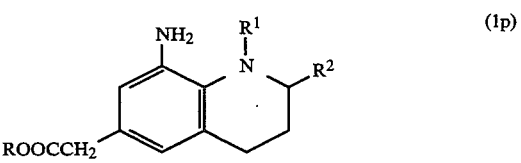

[wherein R, R¹ and R² denote same meanings as above] can be prepared.

Compounds represented by a general formula (1r)

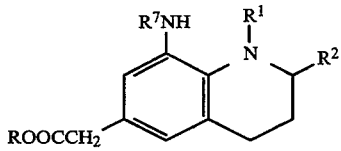
(1r)

[wherein R, R¹ and R² are same as above and R⁷ denotes a lower alkanoyl group having 1 to 3 carbon atoms, benzoyl group which may be substituted, lower alkylsulfonyl group having 1 to 3 carbon atoms or phenylsulfonyl group which may be substituted] can be prepared by reacting the compounds represented by the general formula (1p) with compounds represented by a general formula (1q)

(1q)

[wherein $R^7$ is same as above and Y denotes a halogen atom] at room temperature in a suitable solvent, for example, dioxane, dimethyl sulfoxide, dimethylformamide or the like under stirring, using a suitable base, for example, triethylamine, pyridine or the like.

Compounds represented by a general formula (1s)

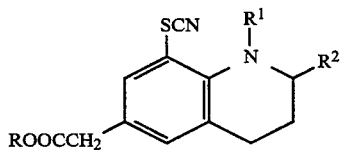
(1s)

[wherein R, R¹ and R² denote same meanings as above] can be prepared by stirring the compounds represented by the general formula (1b) with potassium thiocyanate and bromine at 10° C. to room temperature in a suitable solvent, for example, acetic acid.

Compounds represented by a general formula (1u)

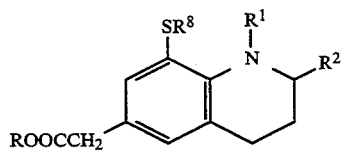
(1u)

[wherein R, R¹ and R² are same as above and R⁸ denotes a lower alkyl group having 1 to 3 carbon atoms] can be prepared by reacting the compounds represented by the general formula (1s) with sodium sulfide in a suitable solvent, for example, methanol, ethanol or the like under heating and stirring to reduce, and successively, by reacting with compounds represented by a general formula (1t)

(1t)

[wherein R⁸ and Y denote same meanings as above].

Compounds represented by a general formula (1v)

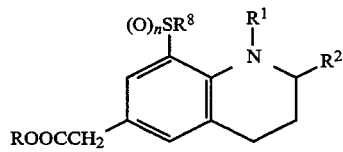
(1v)

[wherein R, R¹, R² and R⁸ are same as above and n denotes 1 or 2] can be prepared by oxidizing the compounds represented by the general formula (1u) with equimolar or excess oxidizing agent such as m-chloroperbenzoic acid, aqueous hydrogen peroxide or sodium perchlorate at 0° C. to room temperature in a suitable solvent, for example, methanol, ethanol, methylene chloride, chloroform or the like.

By oxidation of compounds represented by a general formula (1w)

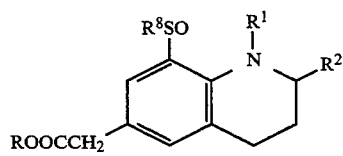
(1w)

[wherein R, R¹, R² and R⁸ denote same meanings as above] with equimolar or excess oxidizing agent, for example, m-chloroperbenzoic acid, aqueous hydrogen peroxide, sodium perchlorate or the like in a suitable solvent, for example, alcohol, methylene chloride, chloroform or the like at room temperature or under heating with stirring, compounds represented by a general formula (1x)

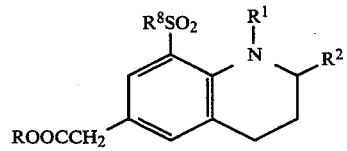
(1x)

[wherein R, R¹, R² and R⁸ denote same meanings as above] can be prepared.

By reacting compounds represented by a general formula (1y)

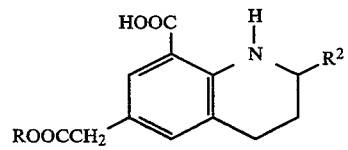
(1y)

[wherein R and R² denote same meanings as above] with formalin in a suitable acid, for example, acetic acid, formic acid, hydrochloric acid or the like under heating and stirring, compounds represented by a general formula (1z)

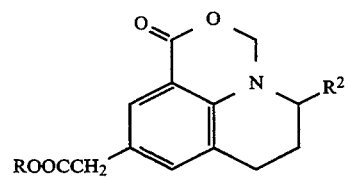
(1z)

[wherein R and R² denote same meanings as above] can be prepared.

Compounds represented by a general formula (1z-a)

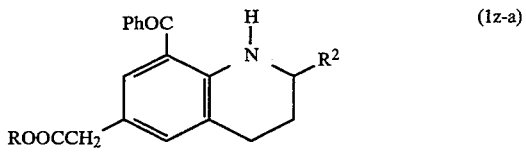

[wherein R and R² denote same meanings as above] can be prepared by reacting the compounds represented by the general formula (1z) with equimolar or slightly excess phenyl lithium at −78° C. to 0° C. in a suitable solvent, for example, tetrahydrofuran, ether or the like under an atmosphere of inert gas, for example, argon or nitrogen.

Moreover, for the inventive compounds represented by the general formula (1), two optical isomers exist, because they have one asymmetric carbon, but the invention includes those optical isomers and racemates.

With respect to the synthesis of optically active substances, by applying, for example, the method of optical resolution against diastereoisomers of tetrahydroquinoline derivatives using N-tosyl-L-proline described in Journal of Medicinal Chemistry, Vol. 30, 839 (1987), the optical isomers of the inventive compounds can be synthesized.

Next, the compounds represented by the general formula (1) can be converted to their salts, for example, salts with hydrochloric acid, sulfuric acid, phosphoric acid, methanesulfonic acid, lactic acid, citric acid, tartaric acid, etc. as acid adducts, and metal salts with sodium, potassium, magnesium, etc. as alkali salts. Best embodiment to put the invention into practice In following, the invention will be illustrated based on concrete examples, but the invention is not confined to these examples.

EXAMPLE 1

Ethyl 2-(2-fluorophenyl)-1,2,3,4-tetrahydroquinoline-6-acetate

Ethyl p-aminophenylacetate (8 g), ethyl 2-fluorobenzoylacetate (10 g) and p-toluenesulfonic acid (1 g) were dissolved into benzene (150 ml) and, providing Dean Stalk dehydrating apparatus placed molecular sieve (MS 4 angstroms) therein, the solution was refluxed for 4.5 hours under heat. Solvent was distilled off under reduced pressure and water was added to the residue, which was extracted with methylene chloride. The organic layer was washed with water, dried over anhydrous sodium sulfate, and then concentrated. After diphenyl ether (60 ml) was added to the residue, the mixture was stirred at 240° to 250° C. for 30 minutes under heat. After cooling, ether was added and the crystals deposited were collected by filtration to obtain crude ethyl 2-(2-fluorophenyl)-4-hydroxyquinoline-6-acetate (9.5 g). After phosphorus oxychloride (40 ml) was added thereto, the mixture was refluxed for 2 hours under heat. After cooling, this was thrown into ice and extracted with methylene chloride. The organic layer was washed with water, dried over anhydrous sodium sulfate, and concentrated to obtain ethyl 4-chloro-2-(2-fluorophenyl)quinoline-6-acetate (9.2 g). This was dissolved into ethanol (200 ml) and, after 10% palladium carbon (1 g) was added, hydrogenation was conducted at a hydrogen pressure of 40 kg/cm² and at 80° C. Catalyst was filtered off, the filtrate was concentrated under reduced pressure, and the residue was purified by means of silica gel column chromatography (development solvent: methylene chloride) to obtain aimed product (3.7 g) as a pale yellow oily substance.

EXAMPLE 2

Ethyl 1,2,3,4-tetrahydro-2-phenylquinoline-6-acetate

Using ethyl p-aminophenylacetate and ethyl benzoylacetate as starting materials, treatment was made similarly to Example 1 to obtain aimed product.

EXAMPLE 3

Methyl 2-(4-methoxyphenyl)-1,2,3,4-tetrahydroquinoline-6-acetate

Using methyl p-aminophenylacetate and ethyl p-methoxybenzoylacetate as starting raw materials, treatment was made similarly to Example 1 to obtain aimed product.

EXAMPLE 4

Ethyl 8-chloro-2-(2-fluorophenyl)-1,2,3,4-tetrahydroquinoline-6-acetate

The compound (2.4 g) of Example 1 was dissolved into dimethylformamide (30 ml) and, after N-chlorosuccimide (1.1 g) was added, the mixture was stirred at 80° C. for 2 hours under heat. After cooling, ice water was added and the reaction liquor was extracted with methylene chloride. The organic layer was washed with saturated saline solution, dried over anhydrous sodium sulfate and concentrated under reduced pressure. The residue was purified by means of silica gel column chromatography (development solvent: methylene chloride) to obtain aimed product (1.5 g) as a pale yellow oily substance.

| Elemental analysis (%): As $C_{19}H_{19}ClFNO_2$ | | | |
|---|---|---|---|
| | C | H | N |
| Calculated | 65.61 | 5.51 | 4.03 |
| Observed | 65.51 | 5.52 | 3.88 |

EXAMPLE 5

Ethyl 8-chloro-2-phenyl-1,2,3,4-tetrahydroquinoline-6-acetate

The compound (3 g) of Example 2 was treated similarly to Example 4 to obtain aimed product (2.6 g) as a pale yellow oily substance.

EXAMPLE 6

Methyl 8-chloro-2-(4-methoxyphenyl)-1,2,3,4-tetrahydroquinoline-6-acetate

The compound (1.76 g) of Example 3 was treated similarly to Example 4 to obtain aimed product (610 mg) as a pale yellow oily substance.

EXAMPLE 7

8-Chloro-2-(2-fluorophenyl)-1,2,3,4-tetrahydroquinoline-6-acetic acid

The compound (1.4 g) of Example 4 was dissolved into 10% aqueous solution of sodium hydroxide (30 ml) and small quantity of ethanol and the solution was refluxed at 80° C. for 2 hours under heat. After cooling, this was acidified with concentrated hydrochloric acid. The crystals deposited were collected by filtration and recrystallized from ethanol-hexane to obtain aimed product (1.2 g) as pale yellow prismatic crystals. Melting point: 127°–129° C.

| Elemental analysis (%): As $C_{17}H_{15}ClFNO_2$ | | | |
|---|---|---|---|
| | C | H | N |
| Calculated | 63.85 | 4.72 | 4.38 |
| Observed | 63.50 | 4.65 | 4.38 |

EXAMPLE 8

8-Chloro-2-phenyl-1,2,3,4-tetrahydroquinoline-6-acetic acid

The compound of Example 5 was teated similarly to Example 7 to obtain aimed product as white prismatic crystals (recrystallization solvent: ether-hexane). Melting point: 126°–127° C.

| Elemental analysis (%): As $C_{17}H_{16}ClNO_2$ | | | |
|---|---|---|---|
| | C | H | N |
| Calculated | 67.66 | 5.34 | 4.64 |
| Observed | 67.38 | 5.24 | 4.51 |

EXAMPLE 9

8-Chloro-2-(4-methoxyphenyl)-1,2,3,4-tetrahydroquinoline-6-acetic acid

The compound of Example 6 was treated similarly to Example 7 to obtain aimed product as white prismatic crystals (recrystallization solvent: ethyl acetate-hexane). Melting point: 140°–141° C.

| Elemental analysis (%): As $C_{18}H_{18}ClNO_3$ | | | |
|---|---|---|---|
| | C | H | N |
| Calculated | 65.16 | 5.47 | 4.22 |
| Observed | 65.01 | 5.43 | 4.13 |

EXAMPLE 10

2-(2-Fluorophenyl)-1,2,3,4-tetrahydroquinoline-6-acetic acid

The compound of Example 1 was treated similarly to Example 7 to obtain aimed product as white prismatic crystals (recrystallization solvent: ether-hexane). Melting point: 117°–118° C.

| Elemental analysis (%): As $C_{17}H_{16}FNO_2$ | | | |
|---|---|---|---|
| | C | H | N |
| Calculated | 71.56 | 5.65 | 4.91 |
| Observed | 71.80 | 5.64 | 4.83 |

EXAMPLE 11

1-Methyl-2-phenyl-1,2,3,4-tetrahydroquinoline-6-acetic acid

The compound (3 g) of Example 2 was dissolved into acetone and, after methyl iodide (0.8 ml) and potassium hydroxide (3.7 g) were added, the mixture was stirred at 40° C. for 20 hours under heat. After water was added and the reaction mixture was acidified with hydrochloric acid, it was extracted with methylene chloride. The residue obtained by drying methylene chloride layer over anhydrous sodium sulfate and then concentrating under reduced pressure was recrystallized from ethanol-hexane to obtain aimed product (1.25 g) as pale yellow powdery crystals. Melting point: 110°–111° C.

| Elemental analysis (%): As $C_{18}H_{19}NO_2$ | | | |
|---|---|---|---|
| | C | H | N |
| Calculated | 76.84 | 6.81 | 4.98 |
| Observed | 76.76 | 6.77 | 5.02 |

EXAMPLE 12

8-Chloro-1-methyl-2-phenyl-1,2,3,4-tetrahydroquinoline-6-acetic acid

The compound (0.7 g) of Example 11 was added to a mixed liquor of methanol (20 ml) with several drops of concentrated sulfuric acid and the mixture was refluxed for 2 hours under heat. After concentration under reduced pressure, methylene chloride was added to the reaction mixture and washed with water, dried over anhydrous sodium sulfate and then concentrated under reduced pressure to obtain crude methyl ester of 1-methyl-2-phenyl-1,2,3,4-tetrahydroquinoline-6-acetic acid. This was dissolved into dimethylformamide (30 ml) and, after N-chlorosuccimide (0.3 g) was added, the mixture was stirred at 50° C. for 2 hours under heat. The reaction liquor was thrown into ice water and extracted with ether. The organic layer was dried over anhydrous sodium sulfate and then concentrated under reduced pressure to obtain methyl 8-chloro-1-methyl-2-phenyl-1,2,3,4-tetrahydroquinoline-6-acetate (0.74 g; melting point: 78°–80° C.) as pale yellow needle-like crystals. This was added to 10% aqueous solution of sodium hydroxide (30 ml) and the mixture was stirred at 60° C. for 1 hour under heat. After cooling, the reaction liquor was made acidic with concentrated hydrochloric acid and extracted with methylene chloride. The crystals obtained by washing methylene chloride layer with water, drying over anhydrous sodium sulfate and then concentrating under reduced pressure were recrystallized from ethyl acetate-hexane to obtain aimed product (0.5 g) as pale yellow prismatic crystals. Melting point: 111°–112° C.

| Elemental analysis (%): As $C_{18}H_{18}ClNO_2$ | | | |
|---|---|---|---|
| | C | H | N |
| Calculated | 68.46 | 5.75 | 4.44 |
| Observed | 68.19 | 5.90 | 4.42 |

EXAMPLE 13

Methyl 1,2,3,4-tetrahydro-2-trifluoromethylquinoline-6-acetate

Process A

Methyl p-aminophenylacetate (7 g), ethyl trifluoroacetoacetate (8.19 g) and p-toluenesulfonic acid (500 mg) were dissolved into benzene (100 ml) and, providing Dean Stalk dehydrating apparatus placed molecular sieve (MS 4 angstroms) therein, the solution was refluxed for 10 hours under heat. Solvent was distilled off under reduced pressure and the residue was purified by means of silica gel column chromatography (development solvent: ethyl acetate:hexane=1:4) to obtain methyl 3-(4-methoxycarbonylmethylphenylamino)-3-trifluoromethylacrylate (7.18 g) as colorless prismatic crystals. Melting point: 50°-51° C. (recrystallization solvent: ethyl acetate-n-hexane)

| Elemental analysis (%): As $C_{14}H_{14}F_3NO_4$ | | | |
|---|---|---|---|
| | C | H | N |
| Calculated | 53.00 | 4.45 | 4.41 |
| Observed | 52.90 | 4.38 | 4.53 |

To this was added diphenyl ether (30 ml), and the mixture was stirred at about 250° C. for 45 minutes under heat. After cooling, hexane was added and the crystals deposited were collected by filtration and dried to obtain crude methyl 4-hydroxy-2-trifluoromethylquinoline-6-acetate (4.75 g). Melting point: 192°-193° C. (recrystallization solvent: methanol), colorless needle-like crystals

| Elemental analysis (%): As $C_{13}H_{10}F_3NO_3$ | | | |
|---|---|---|---|
| | C | H | N |
| Calculated | 54.74 | 3.53 | 4.91 |
| Observed | 54.39 | 3.47 | 4.92 |

To this were added phosphorus pentachloride (3.81 g) and phosphorus oxychloride (20 ml), and the mixture was stirred at 100° C. for 1 hour. Phosphorus oxychloride was distilled off and water was added to the residue, which was neutralized with sodium bicarbonate. This was extracted with chloroform and the organic layer was washed with water, then with saturated saline solution, dried over anhydrous sodium sulfate and concentrated. The residue was purified by means of silica gel column chromatography (development solvent: ethyl acetate:hexane=1:4) to obtain methyl 4-chloro-2-trifluoromethylquinoline-6-acetate (4.88 g). Melting point: 108°-109° C. (recrystallization solvent: ethyl acetate-n-hexane), white flocky crystals

| Elemental analysis (%): As $C_{13}H_9ClF_3NO_2$ | | | |
|---|---|---|---|
| | C | H | N |
| Calculated | 51.42 | 2.99 | 4.61 |
| Observed | 51.27 | 2.86 | 4.67 |

Methyl 4-chloro-2-trifluoromethylquinoline-6-acetate (12.35 g) thus obtained, triethylamine (5.96 ml) and 10% palladium carbon (600 mg) were added to methanol (200 ml) and the hydrogenation was conducted at a hydrogen pressure of 50 kg/cm² and at room temperature for 3 hours. Catalyst was filtered off and the filtrate was concentrated under reduced pressure. The residue was dissolved by adding ether, washed with water, then with saturated saline solution, dried over anhydrous sodium sulfate and then concentrated to obtain aimed product (10.29 g) as white crystals.

Process B

Into 30 ml of methanol were dissolved 2.17 g (13.2 mmol) of methyl-p-aminophenylacetate, and, under stirring and cooling with ice, a solution of 2.00 g (13.2 mmol) of methyl 3- trifluoromethylpropiolate in 10 ml of methanol was added dropwise. After 30 minutes, solvent was distilled off to obtain methyl 3-(4-methoxycarbonylmethylphenylamino)-3-trifluoromethylacrylate (4.17 g) as a yellow oily substance.

H-NMR (CDCL₃) δ: 3.62(2H, s, CH₂), 3.70, 3.75 (6H, S, CO₂CH₃×2), 5.34 (1H, s,

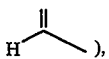), 7.08-7.31 (4H, m, ArH), 9.76 (1H, bs, NH)

When recrystallizing from ethyl acetate-n-hexane, this oily substance becomes colorless prismatic crystals. This was allowed to react successively according to process A to obtain aimed product.

EXAMPLE 14

Methyl 8-chloro-1,2,3,4-tetrahydro-2-trifluoromethylquinoline-6-acetate

The compound (2 g) of Example 13 was treated similarly to Example 4 to obtain aimed product (1.87 g) as a colorless oily substance (purified by means of silica gel column chromatography (development solvent: ethyl acetate:hexane=1:4).

EXAMPLE 15

8-Chloro-1,2,3,4-tetrahydro-2-trifluoromethylquinoline-6-acetic acid

The compound (1.58 g) of Example 14 was added to a mixed liquor of aqueous solution (5 ml) containing sodium hydroxide (310 mg) with ethanol (5 ml) and the mixture was stirred at room temperature for 1 hour. Water (20 ml) was added and the reaction mixutre was brought to pH 4 with concentrated hydrochloric acid, which was extracted with ethyl acetate. The organic layer was dried over anhydrous sodium sulfate and concentrated to obtain aimed product (1.41 g) as white crystals. When recrystallizing from ethyl acetate-hexane, these give a melting point of 127°-128° C.

| Elemental analysis (%): As $C_{12}H_{11}ClF_3NO_2$ | | | |
|---|---|---|---|
| | C | H | N |
| Calculated | 49.08 | 3.78 | 4.77 |
| Observed | 49.09 | 3.72 | 4.70 |

EXAMPLE 16

1,2,3,4-Tetrahydro-2-trifluoromethylquinoline-6-acetic acid

The compound of Example 13 was treated similarly to Example 15 to obtain aimed product as white prismatic crystals (recrystallization solvent: ethyl acetate-hexane). Melting point: 118°-119° C.

| Elemental analysis (%): As $C_{12}H_{12}F_3NO_2$ | | | |
|---|---|---|---|
| | C | H | N |
| Calculated | 55.60 | 4.67 | 5.40 |
| Observed | 55.73 | 4.62 | 5.28 |

EXAMPLE 17

Methyl 1-[N-tosyl-L-prolyl]-1,2,3,4-tetrahydro-2-trifluoromethylquinoline-6-acetate (synthesis of diastereoisomers)

The compound (100 mg) of Example 13 and N-tosyl-L-prolyl chloride (316 mg) were added to anhydrous toluene (0.2 ml) and the mixture was heated at 60° C. for 12 hours and further at 80° C. for 5 hours while stirring. After cooling, the reaction liquor was poured into a saturated aqueous solution of sodium bicarbonate, which was extracted with ethyl acetate. The extracted solution was washed with saturated aqueous solution of sodium bicarbonate and with saturated saline solution, dried over anhydrous magnesium sulfate and concentrated. The residue was purified by means of silica gel column chromatography (development solvent: ethyl acetate:hexane=2:3 to 3:2) to obtain isomer A (83 mg) from early eluted fraction and isomer B (49 mg) from late eluted fraction.

Isomer A: Colorless prismatic crystals (recrystallization solvent; ethyl acetate), Melting point: 204°-205° C.

| Elemental analysis (%): As $C_{25}H_{27}F_3N_2O_5S$ | | | |
|---|---|---|---|
| | C | H | N |
| Calculated | 57.24 | 5.19 | 5.34 |
| Observed | 57.24 | 5.12 | 5.33 |

Isomer B: Colorless foamy substance

| Elemental analysis (%): As $C_{25}H_{27}F_3N_2O_5S$ | | | |
|---|---|---|---|
| | C | H | N |
| Calculated | 57.24 | 5.19 | 5.34 |
| Observed | 57.32 | 5.19 | 5.17 |

EXAMPLE 18

1,2,3,4-Tetrahydro-2-trifluoromethylquinoline-6-acetic acid (+) isomer

The isomer A (56 mg) of Example 17 was added to 20% aqueous solution of sodium hydroxide (5 ml) and the mixture was heated at 100° C. for 3 hours while stirring. Ice pieces were added to the reaction liquor, which was brought to pH 3 to 4 with concentrated hydrochloric acid and extracted with ethyl acetate. The extracted solution was washed with saturated saline solution, dried over anhydrous magnesium sulfate and concentrated. The residue was purified by means of silica gel column chromatography (development solvent: ethyl acetate:hexane=1:1 to ethyl acetate alone) to obtain aimed product (14.9 mg) as colorless flaky crystals (recrystallication solvent; methylene chloride-hexane). Melting point: 107°-108° C.

Specific rotation $[\alpha]_D^{25}$ 17.9° (c=0.223 chloroform)

EXAMPLE 19

1,2,3,4-Tetrahydro-2-trifluoromethylquinoline-6-acetic acid (−) isomer

The isomer B (41 mg) of Example 17 was treated similarly to Example 18 to obtain aimed product (7.8 mg) as colorless flaky crystals (recrystallication solvent; methylene chloride-hexane). Melting point: 105°-107° C.

Specific rotation $[\alpha]_D^{25}$ −15.3° (c=0.222, chloroform)

EXAMPLE 20

8-Chloro-1,2,3,4-tetrahydro-2-trifluoromethylquinoline-6-acetic acid (+) isomer

The compound (14.8 mg) of Example 18 was dissolved into anhydrous N,N-dimethylformamide (0.2 ml) and, after N-chlorosuccimide (8.4 mg) was added thereto, the mixture was heated at 70° C. for 30 minutes in argon stream while stirring. The reaction liquor was dissolved into ethyl acetate (15 ml), which was washed with water and with saturated saline solution, dried over anhydrous magnesium sulfate and concentrated. The residue was purified by means of silica gel column chromatography (development solvent; ethyl acetate:hexane=1:4 to ethyl acetate alone) to obtain aimed product (9.2 mg) as colorless crystals. Melting point: 110°-112° C.

Specific rotation $[\alpha]_D^{25}$ −21.2° (c=0.613, chloroform)

EXAMPLE 21

8-chloro-1,2,3,4-tetrahydro-2-trifluoromethylquinoline-6-acetic acid (−) isomer

The isomer A (7.8 mg) of Example 19 was treated similarly to Example 20 to obtain aimed product (4.5 mg) as colorless crystals. Melting point: 108°-111° C.

Specific rotation $[\alpha]_D^{25}$ −19.3° (c=0.3, chloroform)

EXAMPLE 22

Methyl 8-bromo-1,2,3,4-tetrahydro-2-trifluoromethylquinoline-6-acetate

Into 30 ml of DMF were dissolved 3.18 g of the compound of Example 13, and, under stirring at −5° to 0° C., a solution of 2.07 g of NBS (N-bromosuccimide) in 30 ml of DMF was added dropwise over 1 hour. After dropwise addition, 20 ml of ice water were added to stop the reaction. After 100 ml of water was added further, the reaction mixture was extracted with ethyl acetate (300 ml). The organic layer was washed with water (300 ml×3 times) and with saturated saline solution (150 ml×1) and then dried over anhydrous sodium sulfate. Solvent was distilled off and the residue was purified by means of silica gel column chromatography (development solvent: ethyl acetate:hexane=1:4) to obtain 3.62 g of aimed product as faintly yellow oily substance.

EXAMPLE 23

8-Bromo-1,2,3,4-tetrahydro-2-trifluoromethylquinoline-6-acetic acid

The compound of Example 22 was treated similarly to Example 15 to obtain aimed product as faintly yellow crystals (recrystallization solvent: ethyl acetate-hexane). Melting point: 111°-112° C.

| Elemental analysis (%): As $C_{12}H_{11}BrF_3NO_2$ | | | |
| --- | --- | --- | --- |
|  | C | H | N |
| Calculated | 42.63 | 3.28 | 4.14 |
| Observed | 42.89 | 3.13 | 4.10 |

EXAMPLE 24

8-Cyano-1,2,3,4-tetrahydro-2-trifluoromethylquinoline-6-acetic acid

Into N-methyl-2-pyrrolidone were dissolved 3.42 g of methyl ester of 8-bromo-1,2,3,4-tetrahydro-2-trifluoromethylquinoline-6-acetic acid, and, after 1.06 g of copper cyanide were added, the mixture was stirred at 170° C. After 3 hours, it was cooled to 60° C. and, after 3 g of ferric chloride 6-hydrate, 5 ml of concentrated hydrochloric acid and 20 ml of water were added, the mixture was stirred further at the same temperature for 0.5 hours. Hundred ml of water were added and the reaction mixture was extracted with ethyl acetate (300 ml×2), which was washed with water (500 ml×2), with saturated aqueous sodium bicarbonate (200 ml×1) and with saturated saline solution (200 ml×1) and then dried over anhydrous sodium sulfate. Solvent was distilled off and the residue was purified by means of silica gel chromatography (development solvent; ethyl acetate:hexane=1:2) to obtain 1.94 g of methyl ester of 8-cyano-1,2,3,4-tetrahydro-2-trifluoromethylquinoline-6-acetic acid as a yellow oily substance.

By using 600 mg of this oily substance and conducting similarly to Example 15, 550 mg of aimed product were obtained as yellow crystals. When recrystallizing from ethyl acetate-hexane, this product gives a melting point of 148°–149° C.

| Elemental analysis (%): As $C_{13}H_{11}F_3N_2O_2$ | | | |
| --- | --- | --- | --- |
|  | C | H | N |
| Calculated | 54.93 | 3.90 | 9.86 |
| Observed | 55.03 | 3.78 | 9.72 |

EXAMPLE 25

8-Carbamoyl-1,2,3,4-tetrahydro-2-trifluoromethylquinoline-6-acetic acid

To 10 ml of polyphosphoric acid (phosphoric acid:phosphorus pentoxide=1:1) was added a solution of 1.23 g of methyl ester of 8-cyano-1,2,3,4-tetrahydro-2-trifluoromethylquinoline-6-acetic acid in 2 ml of methanol at 110° C. under stirring. After stirring for 1.5 hours, 100 ml of ice water were added and the reaction mixture was extracted with ethyl acetate (100 ml×2), which was washed with water and with saturated saline solution (100 ml×1) and then dried over anhydrous sodium sulfate. Solvent was distilled off and the residue was purified by means of silica gel chromatography (development solvent; ethyl acetate:hexane=1:2) to obtain 560 mg of methyl ester of 8-carbamoyl-1,2,3,4-tetrahydro-2-trifluoromethylquinoline-6-acetic acid as white crystals. Further, 500 mg of mixture of this carbamoyl form with methyl ester of 8methoxycarbonyl-1,2,3,4-tetrahydro-2-trifluoromethylquinoline-6-acetic acid were obtained as an oily substance.

By treating 560 mg of crystals obtained as a pure product similarly to Example 15, 520 mg of white crystals were obtained. When recrystallizing from ethanol, this product gives a melting point of 217°–219° C.

| Elemental analysis (%): As $C_{13}H_{13}F_3N_2O_3$ | | | |
| --- | --- | --- | --- |
|  | C | H | N |
| Calculated | 51.66 | 4.34 | 9.27 |
| Observed | 51.40 | 4.17 | 9.15 |

EXAMPLE 26

8-Carboxy-1,2,3,4-tetrahydro-2-trifluoromethylquinoline-6-acetic acid

Into 10 ml of ethanol were dissolved 500 mg of mixture of methyl esters of 8-carbamoyl- and 8-methoxycarbonyl-1,2,3,4-tetrahydro-2-trifiuoromethylquinoline-6-acetic acid, and after 10% aqueous solution of sodium hydroxide were added, the mixture was refluxed for 7 hours under heat. After cooling, 50 ml of water were added and the reaction mixture was brought to pH 2. The crystals deposited were collected by filtration, washed with water and dried to obtain 350 mg of white crystals. When recrystallizing from ethyl acetate-hexane, this product gives a melting point of 195°–196° C.

| Elemental analysis (%): As $C_{13}H_{12}F_3NO_4$ | | | |
| --- | --- | --- | --- |
|  | C | H | N |
| Calculated | 51.49 | 3.99 | 4.62 |
| Observed | 51.87 | 3.99 | 4.47 |

EXAMPLE 27

8-Phenyl-1,2,3,4-tetrahydro-2-trifluoromethylquinoline-6-acetic acid

Under argon stream, 1 g of methyl ester of 8-bromo-1,2,3,4-tetrahydro-2-trifluoromethylquinoline-6-acetic acid and 100 mg of tetrakistriphenylphosphine palladium were dissolved into 20 ml of benzene. After a solution of 380 mg of phenylboric acid in small quantity of ethanol and then 2.9 ml of 2M aqueous solution of sodium carbonate were added, the mixture was refluxed for 7 hours under heat. After cooling, 100 ml of water were added and the reaction mixture was extracted with ethyl acetate (100 ml×2), which was washed with saturated saline solution. After drying over anhydrous sodium sulfate, solvent was distilled off and the residue was purified by means of silica gel chromatography (development solvent; ethyl acetate:hexane=1:5). As a result, 880 mg of mixture of raw material with methyl ester of 8-phenyl-1,2,3,4-tetrahydro-2-trifluoromethylquinoline-6-acetic acid were obtained as a colorless oily substance.

This oily substance was dissolved into 20 ml of ethanol and, after 1 ml of triethylamine and 50 mg of 10% palladium carbon were added, the mixture was reduced catalytically at room temperature. After 3 hours, catalyst was filtered off and the filtrate was concentrated. Then, 200 ml of ethyl acetate were added and the reaction mixture was washed with water and with saturated saline solution, which was dried over anhydrous sodium sulfate. After the solvent was distilled off, the residue was purified by means of silica gel chromatography (development solvent; ethyl acetate:hexane=1:4). As a result, 600 mg of pure methyl ester of 8-phenyl-1,2,3,4- tetrahydro-2-trifluoromethylquinoline-6-acetic acid were obtained as a colorless oily substance.

By using 600 mg of this oily substance and treating similarly to Example 15, 510 mg of aimed product were obtained as white crystals. When recrystallizing from ethyl acetate-hexane, this product gives a melting point of 131°–132° C.

| Elemental analysis (%): As $C_{18}H_{16}F_3NO_2$ | | | |
|---|---|---|---|
| | C | H | N |
| Calculated | 64.47 | 4.81 | 4.18 |
| Observed | 64.40 | 4.70 | 4.11 |

EXAMPLE 28

8-Acetyl-1,2,3,4-tetrahydro-2-trifluoromethylquinoline-6-acetic acid

Into 20 ml of dimethylformamide were dissolved 1.15 g of methyl ester of 8-bromo-1,2,3,4-tetrahydro-2-trifluoromethylquinoline-6-acetic acid, 232 mg of bistriphenylphosphine palladium dichloride and 63 mg of copper iodide, and, after 1.9 ml of triethylamine and 0.55 ml of trimethylsilylacetylene were added, the mixture was stirred at 80° C. under heat. After 8 hours, 200 ml of methylene chloride were added to the reaction mixture and washed with water, 10% citric acid, water and saturated saline solution in sequence. After drying over anhydrous sodium sulfate, solvent was distilled off and the residue was purified by means of silica gel chromatography (development solvent; ethyl acetate:hexane=1:4). A mixture of raw material with methyl ester of 1,2,3,4-tetrahydro-2-trifluoromethyl-8-trimethylsilylethinylquinoline-6-acetic acid was obtained as an oily substance.

This mixture was dissolved into 20 ml of 70% water-containing acetone and, after 2.2 g of concentrated sulfuric acid and 890 mg of mercury sulfate were added, the mixture was refluxed under heat. After 5 hours, 100 ml of water was added and the reaction mixture was extracted with ethyl acetate, which was washed with water and with saturated saline solution and then dried over anhydrous sodium sullfate. Solvent was distilled off and the residue was purified by means of silica gel chromatography (development solvent; ethyl acetate:hexane=1:4) to obtain 150 mg of pure methyl ester of 8-acetyl-1,2,3,4-tetrahydro-2-trifluoromethylquinoline-6-acetic acid as a yellow oily substance.

Further, by treating similarly to Example 15, 120 mg of aimed product were obtained in pure form as yellow crystals. When recrystallizing from ethyl acetate-hexane, this product gives a melting point of 173°–174° C.

| Elemental analysis (%): As $C_{14}H_{14}F_3NO_3$ | | | |
|---|---|---|---|
| | C | H | N |
| Calculated | 55.82 | 4.68 | 4.65 |
| Observed | 55.88 | 4.68 | 4.51 |

EXAMPLE 29

8-Methylthio-1,2,3,4-tetrahydro-2-trifluoromethylquinoline-6-acetic acid

Into 25 ml of acetic acid were dissolved 2.5 g of the compound of Example 13 and 1.26 g of potassium thiocyanate, and the solution was stirred at 10° C. To this was slowly added dropwise a solution of 0.35 ml of bromine in 5 ml of acetic acid, and thereafter the mixture was stirred at 15° to 20° C. for 1.5 hours. After ice water was added, the reaction mixture was neutralized with sodium hydrogen-carbonate and extracted with ethyl acetate, which was washed with water and with saturated saline solution and then dried over anhydrous sodium sulfate. Solvent was distilled off and the residue was purified by means of silica gel chromatography (development solvent; ethyl acetate:hexane=1:4) to obtain 1.83 g of 1,2,3,4-tetrahydro-8-thiochyano-2-trifluoromethylquinoline-6-acetic acid as white crystals.

Into 30 ml of ethanol were dissolved 2.97 g of this compound, and, after 2.88 g of sodium sulfide 9-hydrate and 10 ml of water were added, the=mixture was refluxed under heat. After 5 hours, temperature was lowered to 50° C. and, after 5 ml of methyl iodide and 1 g of sodium hydrogen-carbonate were added, the mixture was stirred at the same temperature for 3 hours. After cooling, dilute hydrochloric acid was added to bring to pH 2 and the reaction mixture was diluted by adding water and then extracted with ethyl acetate, which was washed with water and with saturated saline solution and then dried over anhydrous sodium sulfate. Solvent was distilled off and the reside was purified by means of silica gel chromatography (development solvent; from ethyl acetate:hexane=1:3 to methylene chloride:ethanol=10:1). As a result, 1.17 g of methyl ester of 8-methylthio-1,2,3,4-tetrahydro-2-trifluoromethylquinoline-6-acetic acid as a faintly yellow oily substance and 720 mg of 8-methyltio-1,2,3,4-tetrahydro-2-trifluoromethylquinoline-6-acetic acid as white crystals were obtained. When recrystallizing from ethyl acetate-hexane, these crystals give a melting point of 112°–113° C.

| Elemental analysis (%): As $C_{13}H_{14}F_3NO_2S$ | | | |
|---|---|---|---|
| | C | H | N |
| Calculated | 51.14 | 4.62 | 4.59 |
| Observed | 50.94 | 4.53 | 4.53 |

EXAMPLE 30

8-Methylsulfinyl-1,2,3,4-tetrahydro-2-trifluoromethylquinoline-6-acetic acid

Into 30 ml of methylene chloride were dissolved 1.17 g of methyl ester of 8-methylthio-1,2,3,4-tetrahydro-2-trifluoromethylquinoline-6-acetic acid, and the mixture was stirred under cooling with ice. To this were added 870 mg of m-chloroperbenzoic acid and 336 mg of sodium hydrogen-carbonate, and the mixture was stirred for 1 hours. Water was added and the reaction mixture was extracted with methylene chloride, which was washed with saturated aqueous sodium bicarbonate, with water and with saturated saline solution and then dried over anhydrous sodium sulfate. Solvent was distilled off and the residue was purified by means of silica gel chromatography (development solvent; ethyl acetate:hexane=1:1) to obtain 620m g of dia-stereoisomer A and 300 mg of diastereoisomer B of methyl 8-methylsulfinyl-1,2,3,4-tetrahydro-2-trifluoromethylquinoline-6-acetate as white crystals. Moreover, 180 mg of methyl ester of 8-methylsulfonyl-1,2,3,4-tetrahydro-2-trifluoromethylquinoline-6-acetic acid were obtained as white crystals.

By treating 850 mg of sulfinyl form thus obtained similarly to Example 15, white crystals (780 mg) were obtained. When recrystallizing from ethyl acetate, this product gives a melting point of 168°–170° C.

| Elemental analysis (%): As $C_{13}H_{14}F_3NO_3S$ | | | |
|---|---|---|---|
| | C | H | N |
| Calculated | 48.59 | 4.39 | 4.36 |
| Observed | 48.55 | 4.33 | 4.32 |

EXAMPLE 31

8-Methylsulfonyl-1,2,3,4-tetrahydro-2-trifluoromethyl-quinoline-6-acetic acid

Into 20 ml of 1N sodium hydroxide were dissolved 250 mg of 8-methylthio-1,2,3,4-tetrahydro-2-trifluoromethylquinoline-6-acetic acid and 300 mg of 8-methylsulfinyl-1,2,3,4-tetrahydro-2-trifluoromethyl-quinoline-6-acetic acid, and, after 10 ml of 35% aqueous hydrogen peroxide were added, the mixture was stirred at room temperature for 3 hours. To this were added 50 ml of water, and the reaction mixture was brought to pH2 with concentrated hydrochloric acid. The crystals deposited were collected by filtration, washed with water and dried to obtain 220 mg of white crystals. Further, the aqueous layer was extracted with ethyl acetate, dried over anhydrous sodium sulfate and then solvent was distilled off to obtain 360 mg of faintly yellow crystals. When recrystallizing from ethyl acetate, the crystals obtained give a melting point of 124°–125° C.

| Elemental analysis (%): As $C_{13}H_{14}F_3NO_4S$ | | | |
|---|---|---|---|
| | C | H | N |
| Calculated | 46.29 | 4.18 | 4.15 |
| Observe | 46.31 | 4.14 | 4.15 |

EXAMPLE 32

Sodium salt of 8-benzoyl-1,2,3,4-tetrahydro-2-trifluoromethylquinoline-6-acetic acid A mixed liquor of 410 mg of 8-carboxy-1,2,3,4-tetrahydro-2-trifluoromethylquinoline-6-acetic acid, 10 ml of acetic acid and 10 ml of 37% formalin was stirred at 120° C. under heat. After 1.5 hours, 100 ml of ice water were added and the reaction mixture was extracted with ethyl acetate, which was washed with water and with saturated saline solution and then dried over an hydrous sodium sulfate. Solvent was distilled off to obtain 350 mg of 6,7-dihydro-1H,3H,5H-5-trifluoromethylpyrido[3,2,1-ij][3,1]benzoxazine-9-acetic acid-1-one as yellow crystals.

Under argon stream, 350 mg of these crystals were dissolved into 10 ml of anhydrous tetrahydrofuran and the solution was stirred under cooling to −78° C. To this was slowly added dropwise 1.1 ml of 2M-phenyl lithium and further supplemented 0.5 ml of phenyl lithium 0.5 hours later, and the mixture was stirred at the same temperature for 1.5 hours. Ten % aqueous solution of citric acid were added and the reaction mixture was extracted with ethyl acetate, which was washed with water and with saturated saline solution and then dried over anhydrous sodium sulfate. Solvent was distilled off and the residue was purified by means of silica gel chromatography (development solvent; methylene chloride:ethanol=10:1) to obtain 300 mg of 8-benzoyl-1,2,3,4-tetrahydro-2-trifluoromethylquinoline-6-acetic acid as a yellow viscous oily substance. To this oily substance were added 0.83 ml of 1N sodium hydroxide and 5 ml of ethanol, and the mixture was dried up under reduced pressure to obtain aimed product as a yellow amorphous substance. Melting point: 165°–167° C.

| Elemental analysis (%): As $C_{19}H_{15}F_3NO_3Na.3H_2O$ | | | |
|---|---|---|---|
| | C | H | N |
| Calculated | 51.94 | 4.82 | 3.19 |
| Observed | 51.81 | 4.85 | 2.76 |

EXAMPLE 33

8-Nitro-1,2,3,4-tetrahydro-2-trifluoromethylquinoline-6-acetic acid

Into 5 ml of methylene chloride were dissolved 273 mg of the compound of Example 13, and the solution was stirred at 0° C. To this were added dropwise 63 μl of fuming nitric acid, and the mixture was stirred at the same temperature. After 50 minutes, 63 μl of fuming nitric acid were further supplemented and the mixture was stirred for 2 hours in total. After the reaction mixture was neutralized by adding saturated aqueous sodium bicarbonate, it was extracted with methylene chloride, which was dried over anhydrous sodium sulfate. Then, solvent was distilled off and the residue was purified by means of silica gel chromatography (development solvent; ethyl acetate:hexane=1:2). As a result, 180 mg of methyl ester of 8-nitro-1,2,3,4-tetrahydro-2-trifluoromethylquinoline-6-acetic acid were obtained as yellow crystals.

By using 400 mg of this compound and treating similarly to Example 15, 350 mg of aimed product were obtained as yellow crystals. When recrystallizing from ethyl acetate-hexane, this product gives a melting point of 177°–178° C.

| Elemental analysis (%): As $C_{12}H_{11}F_3N_2O_4$ | | | |
|---|---|---|---|
| | C | H | N |
| Calculated | 47.36 | 3.64 | 9.21 |
| Observed | 47.23 | 3.57 | 9.09 |

EXAMPLE 34

8-Amino-1,2,3,4-tetrahydro-2-trifluoromethylquinoline-6-acetic acid

Into 50 ml of ethanol were dissolved 1.15 g of methyl ester of 8-nitro-1,2,3,4-tetrahydro-2-trifluoromethyl-quinoline-6-acetic acid, and after 200 mg of 10% palladium carbon were added, the catalytic reduction was conducted at atmospheric pressure and at ambient temperature. After 2.5 hours, catalyst was filtered off and the filtrate was concentrated to obtain 980 mg of methyl ester of 8-amino-1,2,3,4-tetrahydro-2-trifluoromethyl-quinoline-6-acetic acid as green crystals.

These crystals were treated similarly to Example 15 to obtain aimed product as yellow crystals. When recrystallizing from ethyl acetate , this product gives a melting point of 180°–181° C.

| Elemental analysis (%): As $C_{12}H_{13}F_3N_2O_2$ | | | |
| --- | --- | --- | --- |
| | C | H | N |
| Calculated | 52.56 | 4.78 | 10.21 |
| Observed | 52.43 | 4.78 | 9.81 |

EXAMPLE 35

8-Methanesulfonylamino-1,2,3,4-tetrahydro-2-trifluoromethylquinoline-6-acetic acid Into 15 ml of dioxane were dissolved 490 mg of methyl ester of 8-amino-1,2,3,4-tetrahydro-2-trifluoromethylquinoline-6-acetic acid, and, after 0.28 ml of triethylamine and 0.15 ml of methanesulfonyl chloride were added, the mixture was stirred at room temperature for 2 hours. Water was added and the reaction mixture was extracted with ethyl acetate, which was washed with water and with saturated saline solution and dried over anhydrous sodium sulfate. Solvent was distilled off and the residue was purified by means of silica gel chromatography (development solvent; ethyl acetate:hexane=1:2) to obtain 540 mg of methyl ester of 8-methanesulfonylamino-1,2,3,4-tetrahydro-2-trifluoromethylquinoline-6-acetic acid as a faintly yellow powder.

This powder was treated similarly to Example 15 to obtain aimed product as white crystals. When recrystallizing from ethyl acetate-hexane, this product gives a melting point of 189°–191° C.

| Elemental analysis (%): As $C_{13}H_{15}F_3N_2O_4S$ | | | |
| --- | --- | --- | --- |
| | C | H | N |
| Calculated | 44.32 | 4.29 | 7.95 |
| Observed | 44.51 | 4.27 | 7.91 |

EXAMPLE 36

Methyl 8-methoxy-1,2,3,4-tetrahydro-2-trifluoromethylquinoline-6-acetate

Into 50 ml of methanol were dissolved 2.66 g of methyl ester of 4-amino-3-methoxyphenylacetic acid, and, under stirring and cooling with ice, a solution of 2.07 g of methyl ester of 3-trifluoromethylpropiolic acid in 50 ml of methanol was added dropwise over 30 minutes. Solvent was distilled off immediately to obtain methyl 3-(2-methoxy-4-methoxycarbonylmethylphenylamino)-3-trifluoromethylacrylate as a yellow oily substance.

This oily substance was treated similarly to Example 13 to obtain 3.31 g of methyl ester of 4-chloro-8-methoxy-2-trifluoromethylquinoline-6-acetic acid as faintly yellow crystals.

Further, by reducing similarly to example 1, aimed methyl ester of 8-methoxy-1,2,3,4-tetrahydro-2-trifluoromethylquinoline-6-acetic acid was obtained as a colorless oily substance.

EXAMPLE 37

8-Methoxy-1,2,3,4-tetrahydro-2-trifluoromethylquinoline-6-acetic acid

The methyl ester obtained in foregoing Example 36 was treated similarly to Example 15 to obtain aimed product as white crystals. When recrystallizing from ethyl acetate-hexane, this product gives a melting point of 108°–109° C.

| Elemental analysis (%): As $C_{13}H_{14}F_3NO_3$ | | | |
| --- | --- | --- | --- |
| | C | H | N |
| Calculated | 53.98 | 4.88 | 4.84 |
| Observed | 53.99 | 4.84 | 4.83 |

EXAMPLE 38

Methyl 8-methyl-1,2,3,4-tetrahydro-2-trifluoromethylquinoline-6-acetate

Using 1.00 g of methyl ester of 4-amino-3-methylphenylacetyic acid, the reaction was conducted similarly to Example 36 to obtain methyl 3-(2-methyl-4-methoxycarbonylmethylphenylamino)-3-trifluoromethylacrylate as a yellow oily substance.

Further, by treating similarly to Example 13, 980 mg of methyl ester of 4-chloro-8-methyl-2-trifluoromethylquinoline-6-acetic acid were obtained as whit crystals. Then, this product was reduced similarly to Example 1 to obtain aimed product as a faintly yellow oily substance.

EXAMPLE 39

8-Methyl-1,2,3,4-tetrahydro-2-trifluoromethylquinoline-6-acetic acid

The methyl ester obtained in foregoing Example 38 was treated similarly to Example 15 to obtain aimed product as white crystals. When recrystallizing from ethyl acetate-hexane, this product gives a melting point of 135°–136° C.

| Elemental analysis (%): As $C_{13}H_{14}F_3NO_2$ | | | |
| --- | --- | --- | --- |
| | C | H | N |
| Calculated | 57.14 | 5.16 | 5.13 |
| Observed | 57.18 | 5.12 | 5.18 |

Next, test examples with animals will be shown.

TEST EXAMPLE 1

Inhibitory Effect on Vascular Permeability

Male ddY-strain mice were orally administered with the compound of examples in 5% arabic gum suspension. After 45 minutes, 1% Evans Blue dissolved in saline (0.1 ml/10 g body weight) was injected into tail vein, and immediately, 1% of acetic acid diluted in saline (0.1 ml/10 g body weight) was injected into peritoneal cavity. Thirty minutes later, each mouse was sacrificed and peritoneal cavity was washed with saline (2 ml/10 g body weight). Peritoneal exuded fluid was collected and centrifuged at 3,000 rpm for 10 minutes. The optical density of supernatant was read at 630 nm. The volume of Evans Blue was determined from the calibration curve and the inhibition ratio was calculated. As shown in Table 1, the inventive compounds have remarkable inhibitory action on vascular permeability.

TABLE 1

| Number of example | Dose (mg/kg, p.o.) | Inhibition ratio (%) |
| --- | --- | --- |
| 4 | 100 | 33.1 |
| 7 | 100 | 51.1 |

TABLE 1-continued

| Number of example | Dose (mg/kg, p.o.) | Inhibition ratio (%) |
|---|---|---|
| 8 | 100 | 50.0 |
| 9 | 100 | 16.0 |
| 11 | 100 | 42.7 |
| 12 | 100 | 52.7 |
| 15 | 100 | 29.1 |
| 16 | 100 | 37.3 |
| 23 | 100 | 38.6 |
| 24 | 100 | 25.9 |
| 27 | 100 | 27.0 |
| 28 | 100 | 16.7 |
| 29 | 100 | 18.4 |
| 32 | 100 | 19.7 |
| 33 | 100 | 25.4 |

TEST EXAMPLE 2

Therapeutic Effect on the Adjuvant Arthritis in Rats

Heat-killed Mycobacterium butyricum (0.6 mg/rat) suspended in liquid paraffin was injected intradermally into right hind paw of female SD-strain rats. Test compounds suspended in 0.3% CMC solution were administered orally once a day for 7 days from 14 days to 20 days after the injection of adjuvant. The swelling of non-injected hind paw was measured by the water displacement method. Inhibition ratio on swelling at 18 days, 21 days and 27 days after the injection of adjuvant are shown in Table 2.

As shown in Table 2, the inventive compound have remarkable inhibitory effect on the adjuvant arthritis in SD-strain rats. Furthermore even after the end of administration of the inventive compounds, the therapeutic effect was lasted.

TABLE 2

| Number of example | Dose (mg/kg/day) | Inhibition ratio of swelling (%) | | |
|---|---|---|---|---|
| | | 18 Days | 21 Days | 27 Days |
| 7 | 25 | 6 | 19 | 33 |
| | 50 | 36 | 52 | 50 |
| | 100 | 59 | 64 | 64 |
| 15 | 12.5 | 21 | 36 | 50 |
| | 25 | 39 | 45 | 52 |
| | 50 | 39 | 56 | 58 |

TEST EXAMPLE 3

Effect on IgM Antibody-producing Cells in vitro

The spleen cells of $BDF_1$-strain mice were isolated by finely mincing the spleen, centrifuged, and suspended in medium (RPMI-1640+10% FCS). Each 50 μl of spleen cell suspension ($2 \times 10^7$ cells/ml) and sheep erythrocyte suspension ($1 \times 10^7$ cells/ml) was spread on a 96-well plate. Test compounds were dissolved in DMSO and diluted in medium. Then, 100 μl of medium containing test compounds were added to the 96-well plate. After the plate was incubated at 37° C. for 5 days in 5% $CO_2$ incubator, the number of IgM antibody-producing cells was counted by Jerne method. The results are shown in Table 3.

TABLE 3

| Effect on IgM antibody-producing cells in vitro | | | | |
|---|---|---|---|---|
| Number of example | Concentration (M) | n | IgM-PFC/culture (mean ± S.E.) | Inhibition ratio (%) |
| Reference | — | 6 | 82 ± 15 | — |
| 15 | $2 \times 10^{-6}$ | 6 | 24 ± 3* | 71 |

TABLE 3-continued

| Effect on IgM antibody-producing cells in vitro | | | | |
|---|---|---|---|---|
| Number of example | Concentration (M) | n | IgM-PFC/culture (mean ± S.E.) | Inhibition ratio (%) |
| Reference | — | 6 | 82 ± 15 | — |
| | $5 \times 10^{-5}$ | 6 | 31 ± 9* | 62 |

*$p < 0.01$ (Dunnett's test)

The inventive compounds significantly inhibited the appearance of anti-sheep erythrocyte IgM antibody-producing cells in vitro.

TEST EXAMPLE 4

Effect on IgM Antibody-producing Cells in vivo

To a BALB/c-strain mice were intraperitoneally injected with $5 \times 10^8 / 0.1$ ml of sheep erythrocytes. The test compound was administered orally once a day for 4 days since the erythrocyte injection. On the next day of final administration, the spleen cells were isolated by finely mincing the spleen, centrifuged and suspended in medium (RPMI-1640+10% FCS). The number of IgM antibody-producing cells was counted by Jerne method. The results are shown in Table 4.

TABLE 4

| Effect on IgM antibody-producing cells in vivo | | | | |
|---|---|---|---|---|
| Number of example | Dose (mg/kg/day) | n | IgM-PFC/ spleen ($\times 10^2$) (mean ± S.E.) | Inhibition ratio (%) |
| Reference | — | 7 | 995 ± 55 | — |
| 15 | 12.5 | 7 | 651 ± 49* | 35 |

*$p < 0.05$ (Dunnett's test)

The inventive compound significantly inhibited the appearance of anti-sheep erytyrocyte IgM antibody-producing cells also in vivo.

Utilizability in the Industry

As described above, the compounds of the invention represented by the general formula (1) have a modulating action on the immune response together with a prompt therapeutic effect against the inflammatory model. Despite, they do not exhibit any cyclooxygenase-inhibitory action. Hence, the compounds of the present invention can be useful as therapeutically effective agents not only for rheumatoid arthritis but also for various autoimmune diseases.

We claim:

1. A cyclic aminophenylacetic acid compound having the formula:

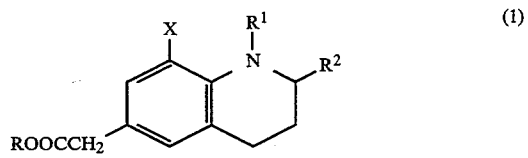

wherein R and $R^1$ are each independently a hydrogen atom or a lower alkyl group, $R^2$ is a phenyl group which is unsubstituted or is substituted with 1 to 3 to groups of halogen atoms, methoxy groups or a combination thereof, or trifluoromethyl groups; and X is a hydrogen atom, a lower alkyl group, lower alkoxy group, cyano group, thiocyano group, trimethylsilylethinyl group, phenyl group which is unsubstituted or substituted by halogen, methoxy, methyl or a combination thereof, carbamoyl, carboxyl, lower alkoxycarbonyl, acetyl, benzoyl, nitro, amino, lower alkanoylamino, benzoylamino, phenylsulfonylamino, lower alkylthio, lower alkylsulfinyl, lower alkylsulfonyl or halogen or optical isomers of salts thereof.

2. An anti-rheumatic agent or a therapeutic agent for autoimmune disease, comprising:

a) an effective amount of a cyclic aminophenylacetic acid compound having the formula:

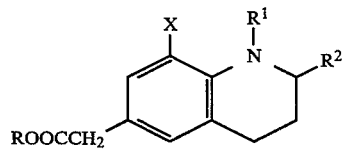

(1)

wherein R and $R^1$ are each independently a hydrogen atom or a lower alkyl group, $R^2$ is a phenyl group which is unsubstituted or is substituted with 1 to 3 to groups of halogen atoms, methoxy groups or a combination thereof, or trifluoromethyl groups; and X is a hydrogen atom, a lower alkyl group, lower alkoxy group, cyano group, thiocyano group, trimethylsilylethinyl group, phenyl group which is unsubstituted or substituted by halogen, methoxy, methyl or a combination thereof, carbamoyl, carboxyl, lower alkoxycarbonyl, acetyl, benzoyl, nitro, amino, lower alkanoylamino, benzoylamino, phenylsulfonylamino, lower alkylthio, lower alkylsulfinyl, lower alkylsulfonyl or halogen or optical isomers of salts thereof; and b) a pharmaceutically-acceptable carrier.

* * * * *